(12) United States Patent
Fischer et al.

(10) Patent No.: US 8,501,679 B2
(45) Date of Patent: Aug. 6, 2013

(54) CYCLIC, CYSTEIN-FREE PROTEIN

(75) Inventors: Bernhard Fischer, Vienna (AT); Rudolf Lucas, Aartselaar (BE)

(73) Assignee: Apeptico Forschung und Entwicklung GmbH, Vienna (AT)

( * ) Notice: Subject to any disclaimer, the term of this patent is extended or adjusted under 35 U.S.C. 154(b) by 350 days.

(21) Appl. No.: 12/747,723

(22) PCT Filed: Dec. 12, 2008

(86) PCT No.: PCT/AT2008/000448
§ 371 (c)(1), (2), (4) Date: Aug. 10, 2010

(87) PCT Pub. No.: WO2009/073909
PCT Pub. Date: Jun. 18, 2009

(65) Prior Publication Data
US 2011/0105414 A1    May 5, 2011

(30) Foreign Application Priority Data

Dec. 12, 2007  (AT) ................. A 2014/2007

(51) Int. Cl.
*A61K 38/00* (2006.01)

(52) U.S. Cl.
USPC .......................................................... 514/1.5

(58) Field of Classification Search
None
See application file for complete search history.

(56) References Cited

U.S. PATENT DOCUMENTS 4,894,439 A    1/1990    Dorin et al.

FOREIGN PATENT DOCUMENTS

| DE | 3841759 A1 | 6/1990 |
| EP | 1 452 868 A2 | 9/2004 |
| WO | 90/06945 | 6/1990 |
| WO | 00/09149 A | 2/2000 |

OTHER PUBLICATIONS

E. A. Carswell, et al "An endotoxin-induced serum factor that causes necrosis of tumors" Proc. Nat. Acad. Sci. USA, vol. 72, No. 9, pp. 3666-3670, Sep. 1957, Immunology.
Bharat B. Aggarwal, et al "Primary Structure of Human Lymphotoxin Derived from 1788 Lymphoblastoid Cell Line" The Journal of Biological Chemistry, vol. 260, Issue Feb. 25, pp. 2334-2344, 1985 USA.
Glen E. Nedwin, et al "Human lymphotoxin and tumor necrosis factor genes: structure, homology and chromosomal localization" Nucleic Acids Research, vol. 13, No. 17, 1985, pp. 6361-6373.
Pierre-François Piguet, et al "Tumor Necrosis Factor/Cachectin is an Effector of Skin and Gut Lesions of the Acute Phase of Graft—vs.—Host Disease" J. Exp. Med. vol. 166, Nov. 1987 pp. 1280-1289.
Marusa Hribar, et al "The lectin-like domain of tumor necrosis factor-α increases membrane conductance in mircrovascular endothelial cells and peritoneal macrophages" Eur. J. Immunol. 1999, 29:3105-3111.
Clemens Braun, et al "Dichotomal Role of TNF in Experimental Pulmonary Edema Reabsorption" J. Immunol. 2005; 175;3402-3408.
Norimasa Fukuda, et al "Mechanisms of TNF-α stimulation of amiloride-sensitive sodium transport across alveolar epithelium" Am J Physiol Lung Cell Mol Physiol 280:L1258-L1265, 2001.
M. T. Clunes, et al "A glucocorticoid-incuded NA+ conductance in human airway epithelial cells identified by perforated patch recording" J Physiol 557.3 (2004) pp. 809-813.
Ahmet Feridun Isik, et al "A new agent for treatment of acute respiratory distress syndrome: thymoquinone. An experimental study in a rat model" European Journal of Cardio-Thoracic Surgery 28 (2005) 301-305.
Michael A. Narachi, Eet al "Role of Single Disulfide in Recombinant Human Tumor Necrosis Factor-α*" The Journal fo Biological Chemistry, vol. 262, No. 27, Sep. 25, 1987, pp. 13107-13110.

*Primary Examiner* — Thomas Heard
(74) *Attorney, Agent, or Firm* — Workman Nydegger

(57) ABSTRACT

A protein selected from the amino acid sequence of the region valine Val(91) to glycine Gly(121) of the mature human tumor necrosis factor, or a portion thereof, with the proviso that the protein comprises at least the amino acid sequence of the region lysine Lys(98) to glutamic acid Glu(116), with the cysteine Cys(101) being replaced by a glycine and an amide bond being formed between the amino group of the side chain of the lysine Lys(98) and the carboxyl group of the side chain of the glutamic acid Glu(116), which activates epithelial ion channels and improves the lung function and which can be used for the manufacture of medicaments for the treatment of diseases associated with the lung function, such as oedemas.

9 Claims, 3 Drawing Sheets

CYCLIC, CYSTEIN-FREE PROTEIN

The present invention relates to a cyclic protein free from cysteines which can be used as a medicament, e.g., for activating epithelial ion channels, for improving the lung function as well as for treating oedemas such as pulmonary oedemas.

The fluid transport through cell layers and tissue is primarily based on an osmotic gradient by an active vectorial ion transport, e.g., sodium transport. It is accomplished mainly by strictly regulated and vitally important ion channels such as, e.g., the epithelial sodium channel complex (ENaC). Water passively follows this gradient, inter alia, through special water channels such as the water channel Aquaporin V. For lung tissue it is known that, basolaterally on the pumping cells, Na+/K+ ATPases drive the vectorial transport of sodium into the interstice and finally of ions into the lymph and blood vessels. Thus, said transport is active and occurs independently of the transpulmonary pressure and the alveolar protein concentration.

An oedema is a pathological accumulation of fluid in an organ such as, e.g., in the lungs, but also in the brain or in the skin. An oedema in the lungs is called a pulmonary oedema. The pulmonary oedema is mostly based on an imbalance between fluid extravasation and fluid resorption. Very often, the permeability of the lung tissue is also damaged so that an increased fluid supply occurs and the fluid accumulates in the pulmonary alveoli.

Such a permeability defect as a result of a lack of return transport of fluid from the pulmonary alveoli into the interstice is particularly significant for an Acute Lung Injury, ALI, or for the Acute Respiratory Distress Syndrome, ARDS, or for the Severe Acute Respiratory Syndrome (SARS), for pneumonia and for multi-organ failure. However, the permeability defect also plays a part in other lung diseases such as respiration-induced lung injuries, lung transplants, transfusion-associated lung injuries, therapeutical administration of IL-2 or asthma.

As a result of an increased fluid accumulation in the tissue or organ, e.g., in the lungs, the required gas exchange is impeded or completely restricted. No oxygen from the breathing air reaches the blood so that life-threatening organ damages may occur due to oxygen deficiency.

There is no general standard therapy for the treatment of the permeability oedema. It is generally attempted to give artificial respiration to patients having pulmonary oedemas in order to ensure the supply of oxygen into the blood and thus into the organs.

Individual peptides derived from the tumour necrosis factor (TNF) are known from DE 38 41 759.

Carswell et al. in Proc. Natl. Acad. Sci. USA 72, 3666, 1975, have reported that the serum of animals treated with endotoxin, which previously had been infected with the mycobacterial strain Calmette-Guerin (BCG), caused haemorrhagic necrosis in different tumours in mice. This activity was attributed to the tumour necrosis factor. TNF also shows a cytostatic or cytotoxic in vitro activity against a plurality of transformed cell lines, whereas normal human and animal cell lines are not affected by this (M. R. Ruff et al, Lymphokines, Vol. II, Academic Press Inc., New York, 1981, pp 235-275). The biochemical characterization and the gene for human TNF has already been described (D Pennica et al, Nature 312, 724, 1984; Aggarwal, B. B. et al, J. Biol. Chem. 260, 2334-2345, 1985; Nedwin, G. E. et al, Nucl. Acids Res. 13, 6361, 1985).

It has been possible to derive the following protein structure for the human mature tumour necrosis factor (TNF) from these data:

($NH_2$)Val Arg Ser Ser Ser Arg Thr Pro Ser Asp Lys Pro Val Ala His Val Val Ala Asn Pro Gln Ala Glu Gly Gln Leu Gln Trp Leu Asn Arg Arg Ala Asn Ala Leu Leu Ala Asn Gly Val Glu Leu Arg Asp Asn Gln Leu Val Val Pro Ser Glu Gly Leu Tyr Leu Ile Tyr Ser Gln Val Leu Phe Lys Gly Gln Gly Cys Pro Ser Thr His Val Leu Leu Thr His Thr Ile Ser Arg Ile Ala Val Ser Tyr Gln Thr Lys Val Asn Leu Leu Ser Ala Ile Lys Ser Pro Cys Gln Arg Glu Thr Pro Glu Gly Ala Glu Ala Lys Pro Trp Tyr Glu Pro Ile Tyr Leu Gly Gly Val Phe Gln Leu Glu Lys Gly Asp Arg Leu Ser Ala Glu Ile Asn Arg Pro Asp Tyr Leu Asp Phe Ala Glu Ser Gly Gln Val Tyr Phe Gly Ile Ile Ala Leu(COOH) (SEQ ID NO:3)

Furthermore, the TNF-gene of cattle, rabbit and mouse has been described (Goeddel D. V. et al., Cold Spring Harbor Symp. Quant. Biol. 51, 597, 1986).

Besides its cytotoxic properties, TNF, amongst others, plays a major part in inflammatory reactions (J. W. Larrick et al, Pharmac. Res. Vol. 5, No. 3, 129-139, 1988). In an animal model, it has been possible to demonstrate the involvement of TNF in septic shock (Torti F. M. et al, Science 229, 867-869, 1985) and in the graft versus host disease (Piguet, P F et al, J. Exp. Med. 166, 1280, 1987).

In Lucas R et al, Science (1994) Vol. 263. no. 5148, pp. 814-817, a peptide is described which has been derived from region Ser(99) to Glu(116) of the TNF and which is suggested for the treatment of oedemas. Said peptide is also the subject matter of WO 00/09149. However, in order to render this peptide of WO 00/09149 usable, position Pro(100) had to be replaced artificially by the amino acid cysteine and position Cys(101) had to be replaced artificially by the amino acid glycine. Since the linear peptide Ser(99) to Glu(116) had no effect according to the invention (Hribar M. et al., Eur. J. Immunol. (1999), Vol. 29, 3105-3111; Braun C., J. Immunol. (2005), 175: 3402-3408; Fukuda N. et al. Am J Physiol Lung Cell Mol Physiol (2001) 280: L1258-L1265), position Glu (116) had to be replaced additionally by the amino acid cysteine.

Such a peptide described in WO00/09149 is unsuitable for the preparation of medicaments since it contains two cysteines in positions (100) and (116) which are known to be reduced in a solution, in which event the sulfur bridge between the cysteines is destroyed and the cyclic structure of the peptide disintegrates, whereby the peptide is rendered ineffective.

Surprisingly, a cyclic peptide free from cysteines has now been found which is derived from the mature tumour necrosis factor (TNF) and exhibits interesting biological properties.

The mature tumour necrosis factor (TNF), as used herein, is preferably the human mature tumour necrosis factor.

In one aspect, the present invention provides a protein which is selected from the amino acid sequence of the region valine Val(91) to glycine Gly(121), or a portion thereof, of the mature human tumour necrosis factor, with the proviso that the protein comprises at least the amino acid sequence of the region lysine Lys(98) to glutamic acid Glu(116), with the cysteine Cys(101) being replaced by a glycine and an amide bond being formed between the amino group of the side chain of the lysine Lys(98) and the carboxyl group of the side chain of the glutamic acid Glu(116).

A protein provided according to the present invention is herein referred to also as a "protein according to (of) the present invention".

According to the present invention, particularly suitable are proteins comprising amino acid sequences SEQ ID:NO:1
(NH$_2$)Val-Asn-Leu-Leu-Ser-Ala-Ile-Lys-Ser-Pro-Gly-Gln-Arg-Glu-Thr-Pro-Glu-Gly-Ala-Glu-Ala-Lys-Pro-Trp-Tyr-Glu-Pro-Ile-Tyr-Leu-Gly(COOH), wherein an amide bond is formed between the amino group of the side chain of the lysine Lys(8) and the carboxyl group of the side chain of the glutamic acid Glu(26), and SEQ ID:NO:2
(NH$_2$)Lys-Ser-Pro-Gly-Gln-Arg-Glu-Thr-Pro-Glu-Gly-Ala-Glu-Ala-Lys-Pro-Trp-Tyr-Glu(COOH), wherein an amide bond is formed between the amino group of the side chain of the lysine Lys(1) and the carboxyl group of the side chain of the glutamic acid Glu(19).

A protein according to the present invention can be produced in a suitable manner, e.g., analogously to a known process, or as described herein, for example, by chemical synthesis by means of peptide chemistry or using microbial processes. The introduction of the amide bond between the free amino group and the free carboxyl group may likewise occur in a suitable manner, e.g., analogously to a known process, or as described herein.

A protein according to the present invention can exist in free form or in the form of a salt, e.g., in the form of an acid addition salt such as an acetate salt or a trifluoroacetic acid salt, and, in a further aspect, the present invention provides a protein according to the present invention in the form of a salt.

It has turned out that a protein according to the present invention shows an interesting biological activity and thus can be used as a medicament.

In a further aspect, the present invention provides a protein according to the present invention for use as a medicament, e.g., the use of a protein according to the present invention as a medicament.

For example, biological examinations on human cells show that a protein according to the present invention, also in contrast to the human TNF, exhibits virtually no inflammatory or toxic properties. For the examination, human immune cells from the blood are mixed with protein according to the present invention at a small concentration and are incubated in a manner common in laboratories. Subsequently, marker proteins for inflammations are determined in cell-free culture media by conventional methods. Despite the addition of a protein according to the present invention, e.g., a protein of amino acid sequence SEQ ID NO:1 or SEQ ID NO:2, such inflammatory proteins, such as, e.g., the inflammation marker Interleukin-6 (IL-6), cannot be detected.

In a further aspect, the present invention provides a process for preventing inflammations, e.g., for preventing the formation of inflammation markers such as IL-6 in the medical application of proteins derived from the tumour necrosis factor, e.g., from the human tumour necrosis factor, which is characterized in that a protein according to the present invention is used.

Furthermore, a method common in laboratories is to detect the activation of ion channels by means of patch-clamp experiments, and this is described, for example, in Clunes M. T. et al, J Physiol Volume 557, No. 3, 809-819 (Jun. 15, 2004). For patch-clamp examinations of ion channels, a glass cannula is stretched thin and filled with a neutral buffer solution. The glass cannula (patch-clamp pipette) is carefully pressed onto an intact epithelial cell. A piece of membrane is located below the pipette. An electrical resistance is thereby produced between the interior of the pipette and the external solution. An electrode attached to a sensitive amplifier dips into the pipette solution.

It surprisingly turns out that a protein according to the present invention, e.g., a protein of amino acid sequence SEQ ID NO:1 or SEQ ID NO:2, which, as described herein, is cyclized by an amide bond, will activate the epithelial ion channels, which is detectable by a variation in the amplitude of the electrical signal. As a result of the fact that a protein according to the present invention contains no cysteine or sulfur bridge, such a protein cannot be reduced.

For the simulation of an acute lung injury and for the formation of a pulmonary oedema, the lungs of laboratory animals, e.g., mice or rats, can be rinsed several times with an acidified saline solution in a manner common in laboratories (for example, according to Isik F. et al., Eur J Cardiothorac Surg (2005); 28: 301-305). The result is a decrease in lung function. If a protein according to the present invention, e.g., a protein of amino acid sequence SEQ ID NO:1 or SEQ ID NO:2, which, as described herein, is cyclized by an amide bond, is injected as a fog or in an aqueous solution into the lungs of the laboratory animals, a distinct improvement in the lung function will occur within 3 to 5 hours, as indicated by the increased oxygen content in the arterial blood.

Thus, a protein according to the present invention can be used for the treatment of oedemas such as pulmonary oedemas.

In another aspect, the present invention provides a protein according to the present invention for the treatment of diseases associated with the lung function, e.g., the use of a protein according to the present invention for the manufacture of a medicament for the treatment of diseases associated with the lung function.

The treatment of diseases associated with the lung function includes, for example, the activation of epithelial ion channels, the improvement of the lung function and/or the treatment of oedemas such as pulmonary oedemas, the treatment of Acute Lung Injury, ALI, of Acute Respiratory Distress Syndrome, ARDS, of Severe Acute Respiratory Syndrome (SARS), of pneumonia, in case of multi-organ failure, in case of respiration-induced lung injuries, lung transplants, transfusion-associated lung injuries, therapeutical administration of IL-2 or asthma, e.g., the activation of epithelial ion channels, the improvement of the lung function and/or the treatment of oedemas such as pulmonary oedemas.

In another aspect, the present invention provides a process for the treatment of diseases associated with the lung function, which is characterized in that a sufficient amount of a protein according to the present invention is administered to a patient in need of such a treatment.

A patient, as used herein, includes mammals, e.g., humans.

A protein according to the present invention can be administered in the form of a pharmaceutical preparation.

In another aspect, the present invention provides a pharmaceutical preparation which is characterized in that it comprises a protein according to the present invention, e.g., in combination with at least one pharmaceutically acceptable adjuvant such as carriers or diluents, for example, fillers, binders, flow-conditioning agents, lubricants, flavouring agents, sugar or sweeteners, odorous substances, preservatives, substances having a stabilizing effect, humectants, emulsifiers, solubilizers, salts for regulating the osmotic pressure and/or buffer (mixtures).

The suitable amount of a protein according to the present invention for the treatment of diseases will of course depend strongly on different parameters, for example, the chemical nature and the pharmacokinetics of the protein used, the individual patient, the disease to be treated, the type of application, however, a successful daily dose for larger mammals includes, for example, an amount ranging from 0.0001 g to 1.5 g, e.g., from 0.001 mg/kg body weight to about 20 mg/kg body weight.

The application may occur pulmonarily or parenterally and preferably occurs parenterally. A pharmaceutical preparation according to the present invention can be produced in a suitable manner, e.g., analogously to a known method, e.g., by mixing, granulation, coating, dissolution, lyophilization methods.

EXAMPLE 1

Synthesis of a Protein Comprising Amino Acid Sequence SEQ ID NO:1, Wherein an Amide Bond is Formed Between the Amino Group of the Side Chain of the Lysine Lys(8) and the Carboxyl Group of the Side Chain of the Glutamic Acid Glu(26)

A protein comprising amino acid sequence SEQ ID NO:1 was synthesized fully automatically via Fmoc solid-phase synthesis in the following steps:

| Step | Process | Product |
| --- | --- | --- |
| 1 | coupling of amino acids | peptide (protein) bound to the solid phase |
| 2 | splitting from the solid phase | peptide (protein) in solution |
| 3 | purification | purified peptide (protein) as a TFA-salt |
| 4 | purification/salt exchange | purified peptide (protein) as an acetate salt |
| 5 | analytical examination | purified peptide (protein) |

The cyclization was effected by connecting the epsilon-amino group of the lysine (position 8) to the gamma-carboxyl group of the glutamic acid (position 26), whereby an amide bond was formed. This is effected, for example, by the gamma-carboxyl group of the glutamic group being converted into an active ester via dicyclohexyl carbodiimide (DCC), which active ester subsequently reacts spontaneously with the epsilon-amino group of the lysine, whereby a ring closure is formed in the protein.

Figure 1A:
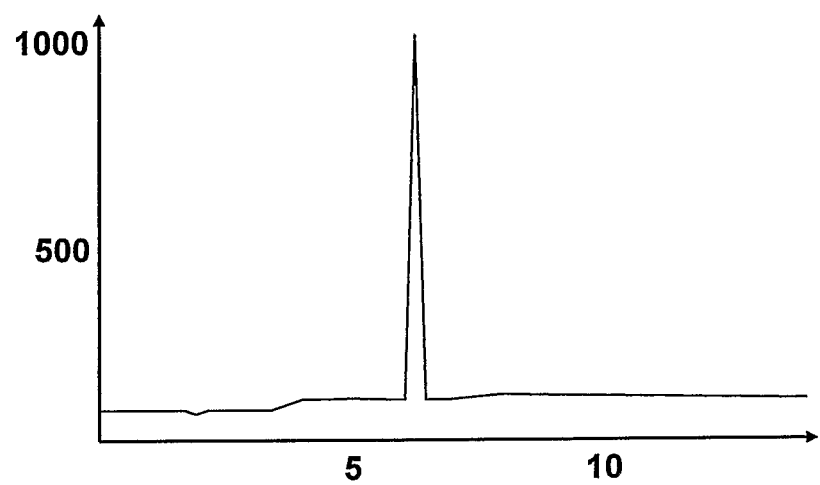
FIG. 1A shows the HPLC chromatogram of the protein comprising amino acid sequence SEQ ID NO:1. Units: y-axis: absorption in mAU; x-axis: time in minutes.

Subsequently, the protein was examined via reverse HPLC, whereby the result as shown in FIG. 1A was obtained.

EXAMPLE 2

Synthesis of a Protein Comprising Amino Acid Sequence SEQ ID NO:2, Wherein an Amide Bond is Formed Between the Amino Group of the Side Chain of the Lysine Lys(1) and the Carboxyl Group of the Side Chain of the Glutamic Acid Glu(19)

A protein comprising amino acid sequence SEQ ID NO:2 was synthesized fully automatically via Fmoc solid-phase synthesis in the following steps:

| Step | Process | Product |
| --- | --- | --- |
| 1 | coupling of amino acids | peptide (protein) bound to the solid phase |
| 2 | splitting from the solid phase | peptide (protein) in solution |
| 3 | purification | purified peptide (protein) as a TFA-salt |
| 4 | purification/salt exchange/ oxidative cyclization | purified peptide (protein) as an acetate salt |
| 5 | analytical examination | purified peptide (protein) |

The cyclization was effected by connecting the epsilon-amino group of the lysine (position 1) to the gamma-carboxyl group of the glutamic acid (position 19), whereby an amide bond was formed. This is effected, for example, by the gamma-carboxyl group of the glutamic group being converted into an active ester via dicyclohexyl carbodiimide (DCC), which active ester subsequently reacts spontaneously with the epsilon-amino group of the lysine, whereby a ring closure is formed in the protein.

Figure 1B:
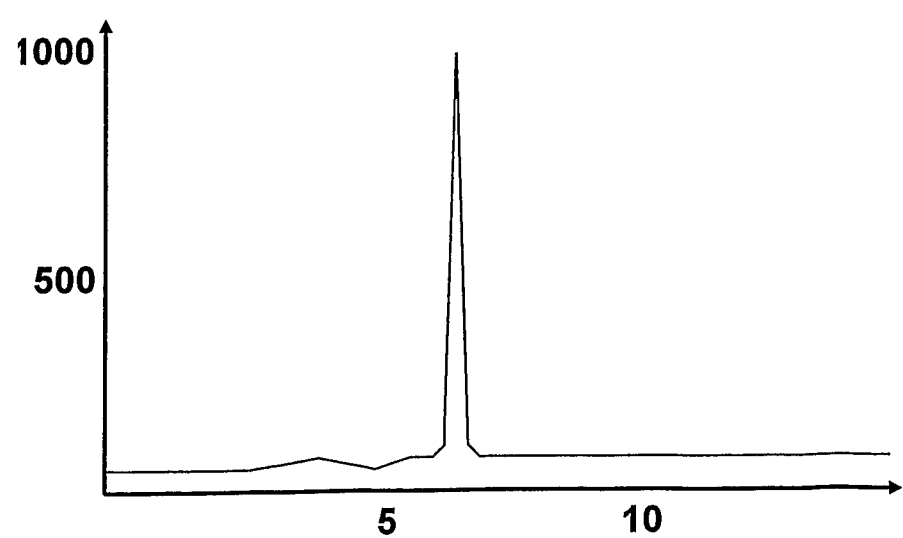
FIG. 1B shows the HPLC chromatogram of the protein comprising amino acid sequence SEQ ID NO:2. Units: y-axis: absorption in mAU; x-axis: time in minutes.

Subsequently, the protein was examined via reverse HPLC, whereby the result as shown in FIG. 1B was obtained.

EXAMPLE 3

Cell Culture

The electrophysiological experiments were performed on human H441 cells. H441 cells are human lung epithelial cells which are involved in the diffusion of water and electrolytes in the lungs.

The H441 cells were obtained from the American Tissue Culture Collection and cultivated in conventional cell culture vessels in RPMI 1640 medium (Invitrogen). The cell culture medium additionally contained 4.5 g/liter glucose, 1% penicillin/streptomycin and 5% fetal calf serum.

For the patch-clamp experiments, the cells were transferred onto small glass plates.

EXAMPLE 4

Activation of Ion Channels of Human Epithelial Cells by Proteins Comprising Amino Acid Sequences SEQ ID NO:1 and SEQ ID NO:2

Macroscopic currents and single-channel currents were discharged from H441 cells in the "whole cell" and "cell-attached" configuration of the "patch-clamp" technique (Hamill et al, Pflugers Arch. 1981, 391(2):85-100, 1981).

For the measurement of individual ion channels, the proteins were dissolved in a solution of 135 mM Na-gluconate, 15 mM NaCl, 5 mM KCl, 1 mM $MgCl_2$, 2 mM $CaCl_2$, 5 mM glucose, 10 mM Hepes, pH 7.4, and filled into the patch pipette. The cell membrane potential was depolarized to 0 mV using the depolarization solution made of 140 m KCl, 15 mM NaCl, 5 mM MgCl$_2$, 10 mM Hepes, pH 7.4. During the measurements, a voltage (patch) of −100 V was adjusted.

This protocol was carried out by adding proteins comprising amino acid sequence SEQ ID NO:1 or SEQ ID NO:2 as well as the sodium channel inhibitor amiloride. The current dissipations thus obtained were stored and analyzed by means of the program PCLAMP 6.0.

Figure 2A:
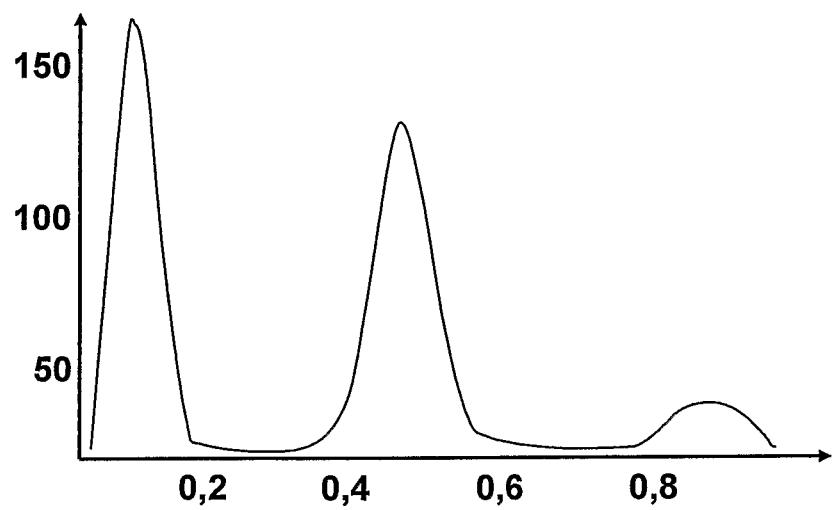
FIG. 2A shows the activation of sodium ion channels by a protein of amino acid sequence SEQ ID NO:1. Units: y-axis: number; x-axis: amplitude in pA.
Figure 2B:
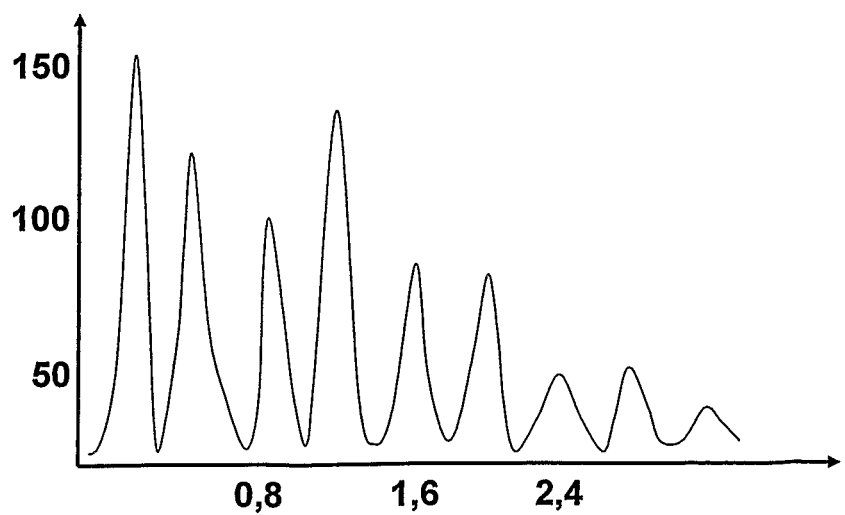
FIG. 2B shows the activation of sodium ion channels by a protein of amino acid sequence SEQ ID NO:2. Units: y-axis: number; x-axis: amplitude in pA.

The results in which the activation of the sodium ion channels by the proteins comprising amino acid sequences SEQ ID NO:1 and SEQ ID NO:2 is shown are evident from FIG. 2A and FIG. 2B.

EXAMPLE 5

Experimental Animal Study Pulmonary Oedema

Male Wistar rats (weighing from 250 g to 350 g) are anesthetized with Rompun® (0.02 ml/100 g) and Ketavet® (0.1 ml/100 g). The respiration is done with a cycle of 72 blows/minute, with an inhalation time of 0.2 seconds and an exhalation time of 0.5 seconds. The body temperature ranges, on average, from 37° C. to 39° C. Under normal conditions, the PaO2 (arterial oxygen partial pressure) ranges from 500 to 550 mm Hg.

For the simulation of an acute lung injury and for the formation of a pulmonary oedema, the lungs are rinsed 7 to 9 times with an acidified saline solution (pH 5).

After one hour, the proteins comprising amino acid sequence SEQ ID NO:1 or SEQ ID NO:2, dissolved in sterile saline solution, are administered intratracheally as a fog (maximum volume administered: 0.5 ml).

At intervals of 60 minutes each, arterial blood (0.1 ml) is withdrawn from the animals, and the oxygen content is determined in % relative to the normal value.

Figure 3A:
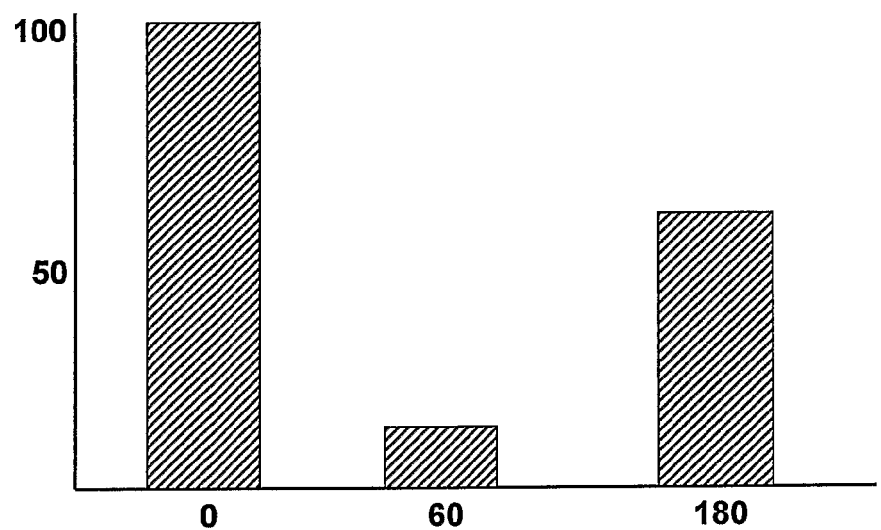
FIG. 3A shows the increase in the oxygen content in the arterial blood upon administration of a protein comprising amino acid sequence SEQ ID NO:1. Units: y-axis: oxygen content in %; x-axis: measuring time in minutes.
Figure 3B:
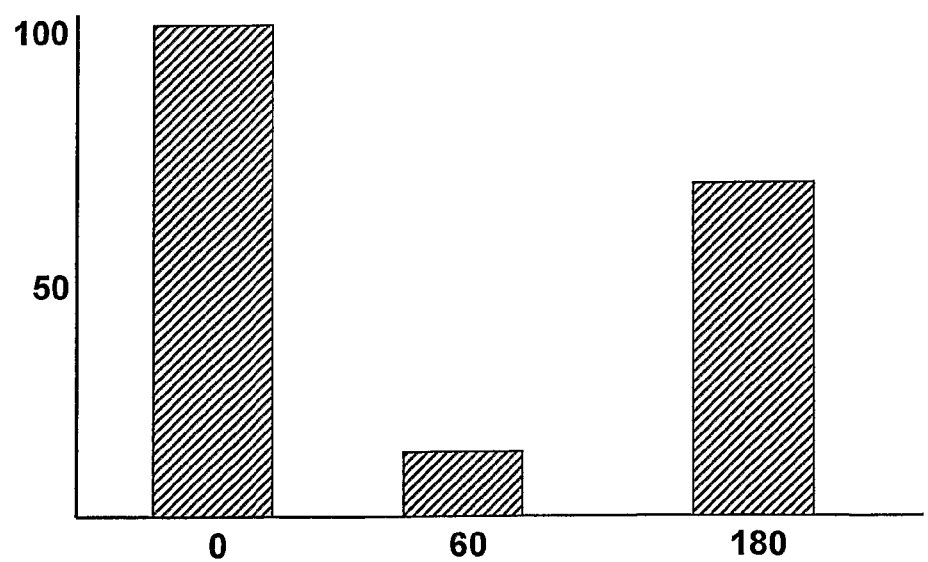
FIG. 3B shows the increase in the oxygen content in the arterial blood upon administration of a protein comprising amino acid sequence SEQ ID NO:2. Oxygen content in %; x-axis: measuring time in minutes.

After administering a protein comprising amino acid sequence SEQ ID NO:1 or SEQ ID NO:2, the oxygen content in the blood is increased, as is evident from FIG. 3A or FIG. 3B, see also Example 6.

EXAMPLE 6

Improvement of the Lung Function by Proteins Comprising Amino Acid Sequences SEQ ID NO:1 and SEQ ID NO:2

The verification of the stimulating effect of a protein according to the present invention, e.g., of a protein comprising amino acid sequence SEQ ID NO:1, SEQ ID NO:2 or SEQ ID NO:3, on the lung function is made via experimental animal studies in which a pulmonary oedema is induced. The experimental procedure is described in Example 5.

For the intratracheal inhalation, 125 µg protein are, in each case, dissolved in 150 mM saline solution pH 7.3. The oxygen content of the arterial blood is measured immediately before rinsing the lungs, 60 minutes after rinsing the lungs and 180 minutes after rinsing the lungs. The oxygen content immediately before rinsing the lungs is determined to be 100%. 60 minutes after the respective final lung rinsing, the oxygen content in the blood amounts to, on average, only 20%. Within 3 hours, the percentage oxygen content rises to values of 62% when the treatment occurs with a protein comprising amino acid sequence SEQ ID NO:1, and 75%, respectively, when the treatment occurs with a protein comprising amino acid sequence SEQ ID NO:2.

Without addition of protein, no improvement in the lung function (oxygen content 20%) will occur within 180 minutes after the lung rinsing.

The results are illustrated in

FIG. 3A for a protein comprising amino acid sequence SEQ ID NO:1,

FIG. 3B for a protein comprising amino acid sequence SEQ ID NO:2.

EXAMPLE 7

Determination of Inflammatory Parameters

Fresh human blood has a very sensitive reaction to pro-inflammatory molecules, among other things, with a release of the inflammation marker Interleukin-6 (IL-6). For determining the pro-inflammatory reaction, samples of human fresh blood at concentrations of the protein comprising amino acid sequence SEQ ID NO:2 were incubated at the following concentrations from 1 ng/ml to 10 µg/ml. After an incubation of 24 hours at 37° C., the inflammation marker Interleukin-6 was quantitatively determined in the solution via ELISA. LPS served as a positive control (concentrations of 3 ng/ml and 100 ng/ml).

In doing so, the measured data, which are indicated in TABLE 1 and which show the influence of the peptide protein comprising amino acid sequence SEQ ID NO:2 in comparison to LPS on the release of the inflammation marker Interleukin-6 from blood cells, were obtained.

TABLE 1

| Concentration of | Protein SEQ ID NO: 2 | Positive control "LPS" |
|---|---|---|
| protein and LPS, respectively | Concentration of Interleukin-6 (pg/ml) (average of three measurements) | |
| without addition of protein (normal blood value) | less than 0.5 | less than 0.5 |
| 10 µg/ml | less than 0.5 | 195.640 |
| 1 µg/ml | less than 0.5 | 108.370 |
| 3 ng/ml | less than 0.5 | 34.867 |
| 1 ng/ml | less than 0.5 | not determined |

The measured data in TABLE 1 show that virtually no inflammation marker IL-6 is released by an incubation of human immune cells in fresh blood with a protein of amino acid sequence SEQ ID NO:2 and that hence no inflammatory reaction is triggered. In contrast, an incubation with LPS as a positive control causes a strong release of the inflammation marker Interleukin-6.

What is claimed is:

1. A protein selected from the amino acid sequence of the region valine Val(91) to glycine Gly(121) of the mature human tumour necrosis factor (SEQ ID NO: 3), or a portion thereof, with the proviso that the protein comprises at least the amino acid sequence of the region lysine Lys(98) to glutamic acid Glu(116), with the cysteine Cys(101) being replaced by a glycine and an amide bond being formed between the amino group of the side chain of the lysine Lys(98) and the carboxyl group of the side chain of the glutamic acid Glu(116).

2. The protein according to claim 1 comprising amino acid sequence SEQ ID:NO:1

(NH$_2$)Val-Asn-Leu-Leu-Ser-Ala-Ile-Lys-Ser-Pro-Gly-Gln-Arg-Glu-Thr-Pro-Glu-Gly-Ala-Glu-Ala-Lys-Pro-Trp-Tyr-Glu-Pro-Ile-Tyr-Leu-Gly(COOH), wherein an amide bond is formed between the amino group of the side chain of the lysine Lys(8) and the carboxyl group of the side chain of the glutamic acid Glu(26) of SEQ ID NO:1.

3. The protein according to claim 1 comprising amino acid sequence SEQ ID:NO:2

(NH$_2$)Lys-Ser-Pro-Gly-Gln-Arg-Glu-Thr-Pro-Glu-Gly-Ala-Glu-Ala-Lys-Pro-Trp-Tyr-Glu(COOH), wherein an amide bond is formed between the amino group of the side chain of the lysine Lys(1) and the carboxyl group of the side chain of the glutamic acid Glu(19) of SEQ ID NO:2.

4. A medicament comprising a protein according to claim 1, optionally in the form of a pharmaceutically acceptable salt.

5. A medicament comprising a protein according to claim 2, optionally in the form of a pharmaceutically acceptable salt.

6. A medicament comprising a protein according to claim 3, optionally in the form of a pharmaceutically acceptable salt.

7. The protein according to claim 1, wherein the protein is in the form of a pharmaceutically acceptable salt.

8. The protein according to claim 2, wherein the protein is in the form of a pharmaceutically acceptable salt.

9. The protein according to claim 3, wherein the protein is in the form of a pharmaceutically acceptable salt.

\* \* \* \* \*

SEQUENCE LISTING

<160> NUMBER OF SEQ ID NOS: 3

<210> SEQ ID NO 1

```
<211> LENGTH: 31
<212> TYPE: PRT
<213> ORGANISM: Artificial
<220> FEATURE:
<223> OTHER INFORMATION: modified peptide derived from the tumour
      necrosis factor (TNF)

<400> SEQUENCE: 1

Val Asn Leu Leu Ser Ala Ile Lys Ser Pro Gly Gln Arg Glu Thr Pro
1               5                   10                  15

Glu Gly Ala Glu Ala Lys Pro Trp Tyr Glu Pro Ile Tyr Leu Gly
            20                  25                  30

<210> SEQ ID NO 2
<211> LENGTH: 19
<212> TYPE: PRT
<213> ORGANISM: Artificial
<220> FEATURE:
<223> OTHER INFORMATION: modified peptide derived from the tumour
      necrosis factor (TNF)

<400> SEQUENCE: 2

Lys Ser Pro Gly Gln Arg Glu Thr Pro Glu Gly Ala Glu Ala Lys Pro
1               5                   10                  15

Trp Tyr Glu

<210> SEQ ID NO 3
<211> LENGTH: 157
<212> TYPE: PRT
<213> ORGANISM: Homo sapiens

<400> SEQUENCE: 3

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```